US011905527B2

(12) United States Patent
Matsui

(10) Patent No.: US 11,905,527 B2
(45) Date of Patent: Feb. 20, 2024

(54) GEL COMPOSITION FOR CULTURING CELLS, PRODUCTION METHOD THEREOF, METHOD FOR CULTURING CELLS, AND SUBSTRATE FOR CULTURING CELLS

(71) Applicant: Shimadzu Corporation, Kyoto (JP)

(72) Inventor: Hayato Matsui, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 960 days.

(21) Appl. No.: 16/482,868

(22) PCT Filed: Feb. 28, 2017

(86) PCT No.: PCT/JP2017/008006
§ 371 (c)(1),
(2) Date: Aug. 1, 2019

(87) PCT Pub. No.: WO2018/142633
PCT Pub. Date: Aug. 9, 2018

(65) Prior Publication Data
US 2020/0231931 A1 Jul. 23, 2020

(30) Foreign Application Priority Data

Feb. 1, 2017 (JP) ................................ 2017-016980

(51) Int. Cl.
C08G 69/08 (2006.01)
C12N 5/00 (2006.01)
C08G 69/44 (2006.01)
C08G 81/00 (2006.01)
C08L 67/04 (2006.01)
C08L 77/00 (2006.01)
C08G 63/06 (2006.01)
C12M 1/12 (2006.01)

(52) U.S. Cl.
CPC ........... C12N 5/0018 (2013.01); C08G 63/06 (2013.01); C08G 69/08 (2013.01); C08G 69/44 (2013.01); C08G 81/00 (2013.01); C08L 67/04 (2013.01); C08L 77/00 (2013.01); C12M 25/18 (2013.01)

(58) Field of Classification Search
CPC ............ A61K 47/6903; B01J 13/0091; C12N 5/0018; C08G 69/08; C08G 69/44; C08L 67/04
See application file for complete search history.

(56) References Cited

U.S. PATENT DOCUMENTS

| 2005/0059150 A1 | 3/2005 | Guarino et al. |
| 2007/0128175 A1 | 6/2007 | Ozbas et al. |
| 2008/0194010 A1 | 8/2008 | Liu |
| 2013/0164266 A1 | 6/2013 | Jensen |
| 2015/0202327 A1* | 7/2015 | Hara ............ A61K 47/593 424/9.6 |
| 2018/0214570 A1* | 8/2018 | Ozeki ............ A61K 47/10 |
| 2019/0105412 A1* | 4/2019 | Hara ............ A61K 9/5153 |

FOREIGN PATENT DOCUMENTS

| CN | 104602680 A | 5/2015 |
| CN | 106220868 A | 12/2016 |
| JP | H05-252944 A | 10/1993 |
| JP | 2006-325461 A | 12/2006 |
| JP | 2007-513603 A | 5/2007 |
| JP | 2009-523118 A | 6/2009 |
| JP | 2010-517590 A | 5/2010 |
| JP | 2013-532966 A | 8/2013 |
| JP | 2015-040276 A | 3/2015 |
| WO | 03/074099 A1 | 9/2003 |
| WO | 2007/059491 A2 | 5/2007 |
| WO | 2008/101001 A2 | 8/2008 |

OTHER PUBLICATIONS

Zhang et al (Effects of immobilizing sites of RGD peptides in amphiphilic block copolymers on efficacy of cell adhesion, Biomaterials 31 (2010) 7873-7882, Available online Jul. 31, 2010).*
International Search Report issued in corresponding International Patent Application No. PCT/JP2017/008006 dated May 16, 2017.
Written Opinion issued in corresponding International Patent Application No. PCT/JP2017/008006 dated May 16, 2017.
Office Action issued in corresponding Chinese Patent Application No. 201780085372.0 dated Nov. 10, 2022.
Office Action issued in corresponding Chinese Patent Application No. 201780085372.0 dated May 10, 2023.
Office Action issued in corresponding Chinese Patent Application No. 201780085372.0 dated Aug. 28, 2023.

* cited by examiner

Primary Examiner — Gregory Listvoyb
(74) Attorney, Agent, or Firm — Morgan, Lewis & Bockius LLP

(57) ABSTRACT

A gel composition contains an amphiphilic block polymer having a hydrophilic block chain and a hydrophobic block chain. An organogel is obtained by mixing the amphiphilic block polymer with an organic solvent, and a xerogel is formed by removing the organic solvent from the organogel. A hydrogel is formed by mixing the xerogel with water or an aqueous solution. A hydrogel encapsulating cells to be cultured may be formed by mixing a xerogel with an aqueous solution containing the cells such as a cell culture solution.

20 Claims, 4 Drawing Sheets

GEL COMPOSITION FOR CULTURING CELLS, PRODUCTION METHOD THEREOF, METHOD FOR CULTURING CELLS, AND SUBSTRATE FOR CULTURING CELLS

TECHNICAL FIELD

The present invention relates to a gel composition used for cell culture of animals and plants, a method for producing the same, and a cell culturing method.

A polystyrene culture plate has been widely used for cell culture of animals and plants. Cells adhere to the plate via adhesion molecules adsorbed on the surface of the plate and adhesion molecules secreted by the cells themselves. At the cell surface, there are receptors that bind to these adhesion molecules, and, via these receptors, signals are input which maintain cell survival and promote proliferation.

When transplanting cells to a living body in regenerative medicine, it is necessary to improve the functions of the cells to a state close to those of the living body. However, in two-dimensional culture on a plate, cells having incomplete functions are often constructed. For two-dimensional culture in which cells are cultured in a monolayer on a plate, a three-dimensional culture technique has been developed in which cells are cultured with a longitudinal thickness. In three-dimensional culture, it has been revealed that cells are likely to express their original functions because the cells interact in many directions and mimic the in vivo state more accurately.

In the three-dimensional culture technique, scaffold substrates (three-dimensional scaffolds) for three-dimensional culture of cells are used. Patent Document 1 proposes a three-dimensional culture technique in which a three-dimensional porous support made of a polymer material such as polystyrene or polyethylene is used as a three-dimensional scaffold.

Techniques using hydrogel as a three-dimensional culture matrix have also been put to practical use. An animal-derived extracellular matrix (ECM)-based hydrogel is commercially available under the trade name "Matrigel", and there are many reports on three-dimensional culture using Matrigel. Patent Document 2 discloses a technology in which a hydrogel formed by self-assembly of a peptide having a specific sequence is used as a three-dimensional culture substrate.

PRIOR ART DOCUMENTS

Patent Documents

Patent Document 1: WO 2008/101001
Patent Document 2: WO 2007/059491

SUMMARY OF THE INVENTION

Problems to be Solved by the Invention

The three-dimensional scaffold consisting of microstructures is difficult to handle and cannot be said to be suitable for mass culture. In addition, since the material is not biodegradable, it is not suitable for transplantation into a living body, and recovery of cells after culture is not easy. Animal-derived ECM-based hydrogels, such as Matrigel, have lot-to-lot variation and can affect cell growth when animal-derived growth factors and the like are included. Therefore, from the viewpoint of quality stability, safety and the like, animal-derived ECM-based hydrogels have little possibility of realization of application to regenerative medicine or the like for the purpose of transplantation into a living body, and the application is limited to in vitro experiments.

The synthetic peptide-based hydrogel disclosed, for example, in Patent Document 2 has a little difference between lots, and is not adversely affected by animal proteins. The hydrogel is degraded by changes in pH, ionic strength, temperature and the like, so that cells cultured using the hydrogel as a scaffold can be recovered. However, it is not easy to prepare a gel so as not to degrade during cell culture and to degrade upon transplantation into a living body, and recovery of cultured cells may be difficult. In addition, since the gel is easily denatured, it is necessary to store the gel under refrigeration or freezing until the time of use, and management is complicated.

As described above, most of the conventional three-dimensional culture substrates have problems such as instability due to lot-to-lot variation, lack of biodegradability, difficulty in recovering cultured cells, complicated storage of culture substrates, etc. In view of these, an object of the present invention is to provide a novel gel composition for cell culture which is applicable as a three-dimensional culture substrate.

Means for Solving the Problems

The present inventor has found that gel compositions based on amphiphilic block polymers have excellent properties as three-dimensional culture substrates. The present invention relates to a gel composition for cell culture having an amphiphilic block polymer having a hydrophilic block and a hydrophobic block, a method for producing the gel composition, and a cell culturing method using the gel composition.

Examples of the amphiphilic block polymer include polysarcosine-polylactic acid block polymers in which the hydrophilic block has 20 or more sarcosine units and the hydrophobic block chain has 10 or more lactic acid units.

The gel composition of the present invention may be a xerogel substantially free of a dispersion medium, or may be a hydrogel containing water as a dispersion medium. An organogel is obtained by mixing the amphiphilic block polymer with an organic solvent, and a xerogel is formed by removing the organic solvent from the organogel. As the organic solvent, for example, an alcohol having 1 to 6 carbon atoms is used. A hydrogel is formed by mixing the xerogel with water or an aqueous solution. The hydrogel preferably contains 10% by weight or more of the amphiphilic block polymer.

A hydrogel encapsulating cells to be cultured may be formed by mixing a xerogel with an aqueous solution containing the cells such as a cell culture solution. For example, a hydrogel which encapsulates cells may be formed by removing an organic solvent from an organogel on a substrate for cell culture such as a well plate to form a xerogel and adding an aqueous solution containing cells onto the culture substrate on which the xerogel has been formed. A substrate for cell culture containing the xerogel on the substrate can be stored at room temperature, and a hydrogel can be obtained by adding water or an aqueous solution onto the xerogel by preparation at the time of use.

The cells after culture in the hydrogel may be recovered by adding water or an aqueous solution to dissolve the gel, or may be transplanted into a living body in a state where the cells are encapsulated in the hydrogel.

Effects of the Invention

The gel composition of the present invention is excellent in stability of quality because it is based on a synthetic polymer having biodegradability. The gel composition of the present invention can be held as a xerogel which is free of a solvent (dispersion medium), and can be stored at normal temperature. The gel composition is easy to handle because a hydrogel to serve as a scaffold for cell culture can be prepared at the time of use by adding a cell culture solution or the like. After the cell culture, the gel is degraded by adding an aqueous solution or the like to adjust the concentration, so that the cells can be easily taken out after the culture. The gel composition of the present invention is useful as a scaffold substance for three-dimensional cell culture.

MODE FOR CARRYING OUT THE INVENTION

Figure 1:
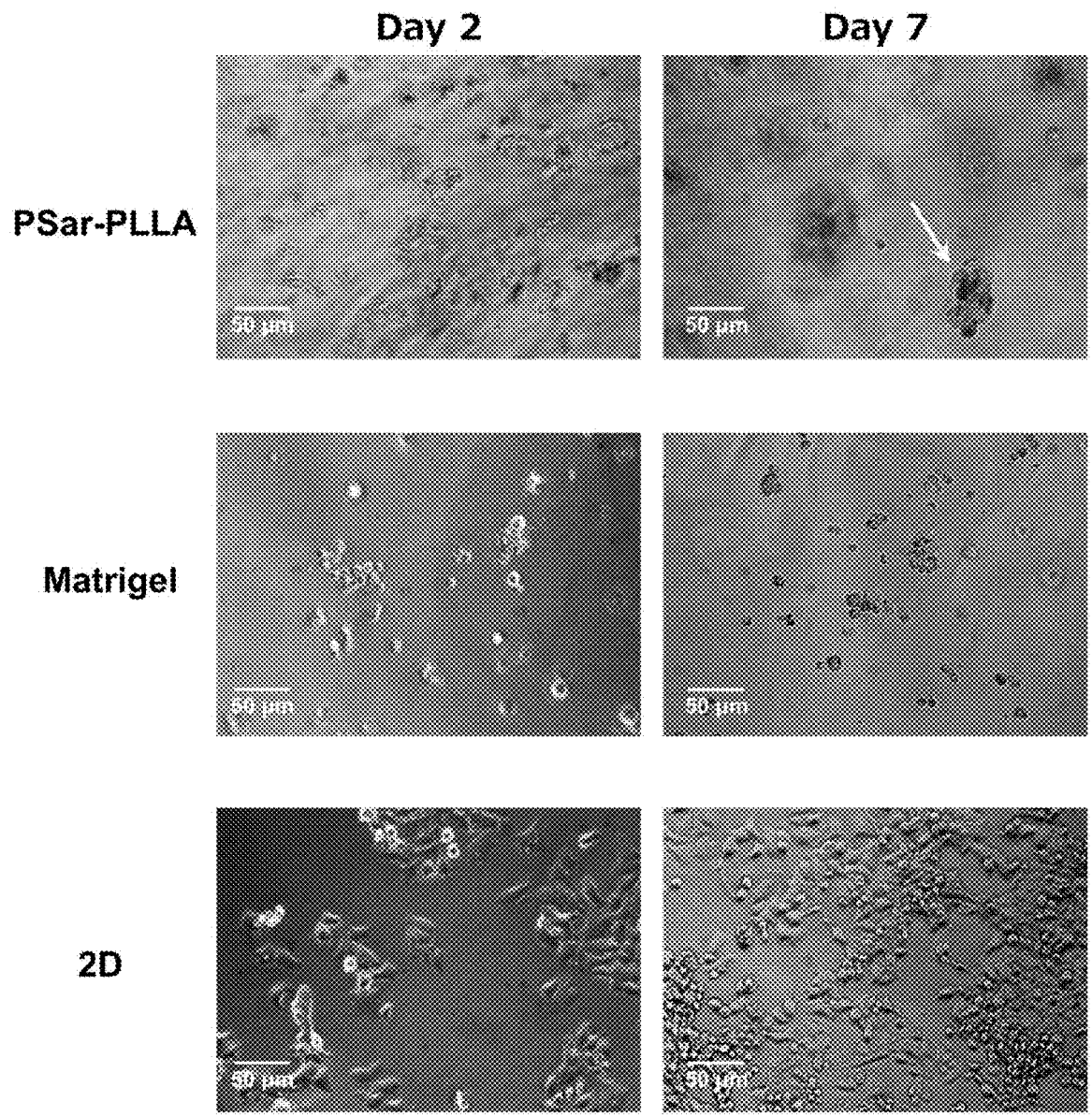
FIG. 1 shows micrographs of Experimental Example 1-2.

A gel composition of the present invention contains an amphiphilic block polymer having a hydrophilic block chain and a hydrophobic block chain. An organogel is obtained by mixing an amphiphilic polymer with an organic solvent such as an alcohol, and a xerogel gel is obtained by removing the organic solvent as a dispersion medium from the organogel. A hydrogel is obtained by mixing the xerogel with water or an aqueous solution.

[Amphiphilic Block Polymer]

The gel composition of the present invention is a composition containing, as a main component, an amphiphilic block polymer having a hydrophilic block chain and a hydrophobic block chain. Examples of the monomer unit of the hydrophilic block chain include alkylene oxide and sarcosine. Examples of the monomer unit of the hydrophobic block chain include hydroxy acids such as glycolic acid, lactic acid and hydroxyisobutyric acid; and hydrophobic amino acids or amino acid derivatives such as glycine, alanine, valine, leucine, isoleucine, proline, methionine, tyrosine, tryptophan, methyl glutamate, benzyl glutamate, methyl aspartate, ethyl aspartate and benzyl aspartate.

Among the amphiphilic block polymers exemplified above, an amphiphilic block polymer having a hydrophilic block chain having a sarcosine unit and a hydrophobic block chain having a lactic acid unit tends to form a gel suitable for cell culture.

(Hydrophobic Block Chain)

The hydrophobic block chain preferably contains 10 or more lactic acid units. Polylactic acid has excellent biocompatibility and stability. In addition, polylactic acid has excellent biodegradability, and thus is metabolized quickly and has low accumulation in a living body. Therefore, amphiphilic polymers having polylactic acid as a constituent block are useful in applications to living bodies, particularly to human bodies. Further, since polylactic acid is crystalline, even when the hydrophobic block chain is short, the hydrophobic block chains are likely to aggregate in a solvent such as an alcohol to form a physical gel.

The upper limit of the number of lactic acid units in the hydrophobic block chain is not particularly limited, but the number of lactic acid units is preferably 1000 or less from the viewpoint of stabilizing the structure. The number of lactic acid units in the hydrophobic block is preferably 10 to 1000, more preferably 15 to 500, and still more preferably 20 to 100.

The lactic acid unit constituting the hydrophobic block chain may be L-lactic acid or D-lactic acid. In addition, L-lactic acid and D-lactic acid may be mixed. In the hydrophobic block chain, all the lactic acid units may be continuous, or the lactic acid units may be discontinuous. The monomer unit other than the lactic acid contained in the hydrophobic block chain is not particularly limited, and examples thereof include hydroxy acids such as glycolic acid and hydroxyisobutyric acid; and hydrophobic amino acids or amino acid derivatives such as glycine, alanine, valine, leucine, isoleucine, proline, methionine, tyrosine, tryptophan, glutamic acid methyl ester, glutamic acid benzyl ester, aspartic acid methyl ester, aspartic acid ethyl ester and aspartic acid benzyl ester.

(Hydrophilic Block Chain)

The hydrophilic block chain preferably contains 20 or more sarcosine units (N-methylglycine units). Sarcosine is highly water soluble. In addition, polysarcosine is capable of cis-trans isomerization because it has an N-substituted amide, and has high flexibility because of less steric hindrance around the alpha carbon. Therefore, by using a polysarcosine chain as a constituent unit, a hydrophilic block chain having both high hydrophilicity and flexibility is formed.

If the number of sarcosine units in the hydrophilic block chain is 20 or more, the hydrophilic blocks of the adjacent block polymers are easily aggregated with each other, so that a gel in which a hydrophilic dispersion medium such as water or an alcohol is incorporated is easily formed. The upper limit of the number of sarcosine units in the hydrophilic block chain is not particularly limited. The number of sarcosine units in the hydrophilic block chain is preferably 300 or less from the viewpoint of aggregating the hydrophobic blocks of the amphiphilic polymers of the adjacent block polymers to stabilize the structure of the gel. The number of sarcosine units is more preferably 25 to 200, and still more preferably 30 to 150.

In the hydrophilic block chain, all the sarcosine units may be continuous, or the sarcosine units may be discontinuous as long as the characteristics of polysarcosine described above are not impaired. When the hydrophilic block chain has a monomer unit other than sarcosine, the monomer unit other than sarcosine is not particularly limited, and examples thereof include hydrophilic amino acids or amino acid derivatives. The amino acids include α-amino acids, β-amino acids and γ-amino acids, and are preferably α-amino acids. Examples of hydrophilic α-amino acids include serine, threonine, lysine, aspartic acid and glutamic acid. In addition, the hydrophilic block may have a sugar chain, a polyether or the like. The hydrophilic block preferably has a hydrophilic group such as a hydroxyl group at the end (the end opposite to the linker with the hydrophobic block).

(Structure and Synthesis Method of Amphiphilic Block Polymer)

The amphiphilic polymer is obtained by binding a hydrophilic block chain and a hydrophobic block chain. The hydrophilic block chain and the hydrophobic block chain may be bound via a linker. As the linker, those having a lactic acid monomer (lactic acid or lactide) which is a constituent unit of the hydrophobic block chain or a functional group (for example, a hydroxyl group or an amino group) capable of binding to a polylactic acid chain and a sarcosine monomer (for example, sarcosine or N-carboxysarcosine anhydride) which is a constituent unit of the hydrophilic block or a functional group (for example, an amino group) capable of binding to polysarcosine are preferably used. By selecting the linker appropriately, the branched structures of the hydrophilic block chain and the hydrophobic block chain can be controlled.

The method for synthesizing the amphiphilic block polymer is not particularly limited, and known peptide synthesis methods, polyester synthesis methods, depsipeptide synthesis methods and the like can be used. In particular, amphiphilic block polymers can be synthesized with reference to WO 2009/148121 and the like.

In order to adjust the hardness, stability, degradability (solubility), etc. of the gel, it is preferred to adjust the chain length of the hydrophobic block chain (number of lactic acid units) and the chain length ratio of the hydrophobic block chain to the hydrophilic block chain (ratio of the number of lactic acid units to the number of sarcosine units). In order to facilitate control of the chain length of the hydrophobic block chain, it is preferable to first synthesize a hydrophobic block chain (for example, polylactic acid) having a linker introduced at one end and then to introduce a hydrophilic block chain (for example, polysarcosine), in the synthesis of the amphiphilic block polymer. The chain lengths of the hydrophobic block chain and the hydrophilic block chain can be adjusted by adjusting the conditions such as the charging ratio between the initiator and the monomer in the polymerization reaction, the reaction time, and the temperature. The chain lengths of the hydrophilic block chain and the hydrophobic block chain (molecular weight of the amphiphilic block polymer) can be confirmed, for example, by $^1$H-NMR. From the viewpoint of enhancing the biodegradability of the amphiphilic polymer, the weight average molecular weight is preferably 10000 or less, more preferably 9000 or less. The amphiphilic polymer used in the present invention may form chemical crosslinks between molecules for the purpose of promoting gel formation, improving the stability of the gel, and the like.

[Preparation of Gel Composition]

A gel is obtained by mixing the above-described amphiphilic polymer with a solvent. In order to form a highly stable gel, it is preferable to mix the amphiphilic polymer and an organic solvent to prepare an organogel and to remove the solvent from the organogel to thereby prepare a substantially solvent-free xerogel. By mixing the xerogel with water or an aqueous solution, a hydrogel suitable for cell culture can be obtained.

As the organic solvent for forming an organogel, a solvent which easily dissolves the hydrophilic block chain of the amphiphilic polymer and which hardly dissolves the hydrophobic block chain is preferable. For example, for an amphiphilic block polymer containing polylactic acid as a hydrophobic block chain and containing polysarcosine as a hydrophilic block chain, an organic solvent which dissolves polysarcosine and does not dissolve polylactic acid is preferably used. By using such an organic solvent, the hydrophobic block moieties of the amphiphilic polymer are aggregated under the mixture of the amphiphilic polymer and the organic solvent, so that a physically crosslinked matrix is easily formed. In addition, if an organogel is formed using such an organic solvent, the xerogel after removal of the organic solvent also tends to have a structure in which the hydrophobic block moieties are aggregated. Therefore, it is considered that, when the xerogel is brought into contact with water or an aqueous solution, water easily penetrates the hydrophilic block chain portion, so that a hydrogel maintaining a polymer matrix structure similar to that of the organogel is easily formed.

The organic solvent used to form the organogel is preferably an alcohol having 1 to 6 carbon atoms. Among them, an alcohol having 1 to 4 carbon atoms is preferable because it highly dissolves the hydrophilic block chain and facilitates the formation of a xerogel by removal of the organic solvent. Specific examples of preferred organic solvents include methanol, ethanol, propanol, 2-propanol, butanol, and 2-butanol.

Two or more organic solvents may be used as a mixture. The solubility of the hydrophobic block chain or the hydrophilic block chain may be adjusted by mixing two or more organic solvents. Also, after dissolution of the amphiphilic polymer using an organic solvent with high dissolution property, an organic solvent with low dissolution property for the hydrophobic block chain is added to promote physical crosslinking by aggregation of the hydrophobic blocks, thereby making it possible to also form a gel matrix. When two or more organic solvents are used, it is preferable that at least one be the above-described alcohol. Two or more alcohols may be used. When the organic solvent is a mixed solvent of two or more organic solvents, it is preferable that 50% by weight or more of the total amount of the organic solvents be occupied by the above-described alcohol. The amount of the alcohol based on the total amount of the organic solvents is more preferably 60% by weight or more, further more preferably 70% by weight or more.

The ratio of the amphiphilic polymer to the organic solvent is not particularly limited, and may be set within the range in which the amphiphilic polymer can be dissolved or swollen depending on the molecular weight of the amphiphilic polymer, the type of the organic solvent, and the like. The amount of the organic solvent is preferably 100 to 1500 parts by weight, more preferably 200 to 1000 parts by weight based on 100 parts by weight of the amphiphilic polymer, from the viewpoint of appropriately maintaining the distance between the adjacent amphiphilic polymers and suppressing gel formation. The content of the amphiphilic block polymer in the organogel composition is preferably 10% by weight or more.

In the formation of an organogel, it is preferable to allow the amphiphilic polymer and the organic solvent to coexist under heating to dissolve or swell the amphiphilic block polymer in an organic solvent, thereby preparing a viscous liquid having fluidity. The molecular motion of the polymer is activated by heating, thereby promoting swelling or dissolution of the amphiphilic polymer by the organic solvent. Any heating temperature in the range not higher than the boiling point of the solvent may be employed, and the heating temperature is for example about 50 to 95° C., preferably about 60 to 90° C. When the solution or swelling product of the amphiphilic block polymer is cooled below the gelation point, the formation of physical crosslinks by the hydrophobic block chain is promoted, so that a low-fluidity (or non-fluidity) organogel is obtained.

By removing the organic solvent as a dispersion medium from the organogel, a xerogel (dry gel) is obtained. The method of removing the organic solvent from the organogel is not particularly limited, and includes a method of precipitating the gel by contact with a nonsolvent, drying with a gas such as nitrogen, vacuum drying, heat drying, heating vacuum drying, freeze drying, and supercritical drying. For the purpose of promoting removal of the organic solvent, the organogel may be pulverized into particles, and then the solvent may be removed. Alternatively, the gel may be pulverized during removal of the solvent.

The degree of removal of the organic solvent is not particularly limited, but it is preferable to remove the solvent until it becomes a solid having no wettability. Preferably, the xerogel is substantially free of a dispersion medium. The content of the dispersion medium in the xerogel is preferably 20% by weight or less, more preferably 10% by weight or less, still more preferably 5% by weight or less based on the total amount of the gel composition. By sufficiently removing the organic solvent in the formation of a xerogel from the organogel, it is possible to reduce the content of the organic solvent in the hydrogel formed from the xerogel, thereby reducing toxicity to cells and also enhancing biosafety.

A hydrogel is obtained by mixing the xerogel with water or an aqueous solution. The method of mixing and wetting the xerogel with water or an aqueous solution is preferable because formation of a hydrogel is easy and the residual organic solvent can be reduced. Moreover, the physical crosslink structure at the time of organogel formation can be easily maintained in a xerogel obtained by removing the solvent from the organogel, and the physical crosslink structure can also be easily maintained even in a hydrogel wetted by contacting the xerogel with water or an aqueous solution, and thus the gel stability is excellent.

As an aqueous solution used in forming a hydrogel from xerogel, a biochemically and pharmaceutically acceptable aqueous solution such as distilled water for injection, a phosphate buffered saline, a buffer or the like is preferably used. An aqueous solution containing cells, such as a cell suspension, may be added to the xerogel to form a hydrogel. The hydrogel formed using the aqueous solution containing cells can be used as it is for cell culture. In this case, there is no need to transplant cells in the gel, and the cells can be dispersed in the gel, so that the workability is excellent.

The gel composition may contain various substances used for cell culture. Substances used for cell culture include various inorganic salts, carbohydrates, amino acids, vitamins, fatty acids, lipids, proteins, and peptides. Also, cell adhesion epitopes, receptor agonists, receptor antagonists, ligands, extracellular matrix components and the like may be included in the gel composition. The amphiphilic polymer may be modified with functional groups having these functions. The gel composition may contain a preservative, a plasticizer, a surfactant, an antifoaming agent, a stabilizer, a buffer, a pH adjusting agent, an osmotic pressure adjusting agent, a tonicity agent, etc.

In the preparation of the hydrogel, the ratio of the amphiphilic polymer to water is not particularly limited, and may be set within the range in which the gel can be wet depending on the molecular weight, mass and the like of the amphiphilic polymer. The amount of water in the hydrogel is preferably 50 to 1500 parts by weight, more preferably 100 to 1000 parts by weight based on 100 parts by weight of the amphiphilic polymer, from the viewpoint of appropriately maintaining the intermolecular distance of the adjacent amphiphilic block polymers and maintaining the strength of the gel. The content of the amphiphilic block polymer in the hydrogel composition is preferably 10% by weight or more.

After formation of the hydrogel, the water may be removed to form a xerogel. For example, when a substance insoluble in the organic solvent or a substance which is easily degraded by the organic solvent is included in the gel composition, a xerogel containing the substance is obtained by removing water after mixing the substance in the hydrogel. The obtained xerogel is wetted again with water or an aqueous solution to obtain a hydrogel.

From the viewpoint of reducing the toxicity and irritation to a living body, the content of the organic solvent in the hydrogel is preferably as low as possible. The proportion of water in the entire dispersion medium of the hydrogel is preferably 80% by weight or more, more preferably 90% by weight or more, still more preferably 95% by weight or more, particularly preferably 98% by weight or more. In order to reduce the content of the organic solvent, it is preferable to increase the removal rate of the organic solvent when forming the xerogel from the organogel. In addition, the content of the organic solvent can also be reduced by repeatedly performing the formation of the hydrogel and the formation of the xerogel by removal of the dispersion medium, after formation of the xerogel from the organogel as described above.

If the organic solvent is removed from the organogel on a substrate such as a well plate, a substrate for cell culture including a xerogel on the substrate can be obtained. For example, the solvent may be removed after the amphiphilic polymer may be dissolved in the organic solvent and then dropped, in a fluid state, onto the well. Also, water may be removed from the hydrogel on the substrate to form a xerogel. By removing the solvent on the substrate, the xerogel fixedly adheres on the substrate surface, which facilitates storage and handling of the culture substrate. A hydrogel encapsulating cells can be formed by adding an aqueous solution containing the cells on a culture substrate on which a xerogel has been formed.

The xerogel can be stored also at room temperature and does not have to be managed under refrigeration or freezing. Therefore, the substrate for cell culture including a xerogel on a substrate can also be stored at room temperature. In this form, handling of a sample is easy because a hydrogel is obtained by adding water or an aqueous solution onto the xerogel by using at the time of preparation. In addition, when an aqueous solution containing cells to be cultured, such as a cell culture solution, is added to the xerogel on the substrate, a hydrogel encapsulating the cells can be obtained, so that drastic improvement in workability can be expected.

[Application of Gel Composition]

The gel composition for cell culture of the present invention is used to culture various cells. In the cell culturing method of the present invention, cell culture is performed in a state where cells to be cultured are encapsulated in a hydrogel. Examples of the method of encapsulating the cells in a hydrogel include a method of injecting a solution containing the cells to be cultured, such as a cell suspension, into a hydrogel. As described above, an aqueous solution containing the cells, such as a cell suspension, and the xerogel may be mixed to form a hydrogel encapsulating the cells. This method does not require the operation of injecting the cells into the hydrogel and is excellent in workability. It is also possible to disperse the cells uniformly in the hydrogel.

The type of cells is not particularly limited, and non-human animal cells, human cells, stem cells, osteoblasts, fibroblasts and the like can be applied. Cell culture using the gel composition may be either two-dimensional culture or three-dimensional culture. When the gel composition of the present invention is used as a scaffold substrate for three-dimensional culture, cell spheroids can grow in an environment closer to that of a living body, and enhanced functionalization of cultured cells can be realized. In addition, the gel composition of the present invention is based on a biodegradable synthetic polymer and does not utilize an animal-derived material, so it is excellent in quality stability and safety, and can be applied to living bodies such as humans. Application of the gel composition in the cell culture field including regenerative medicine is expected.

The conditions for cell culture are not particularly limited, and general cell culture conditions can be applied. The cells after culture may be transplanted to a living body in a state of being encapsulated in the gel composition, or the gel may be degraded to recover the cells after culture. As described above, the amphiphilic block polymer which serves as the base of the gel composition has biodegradability and hardly exhibits toxicity even when transplanted in a living body. If the gel composition of the present invention is used, it is possible to transplant the cell spheroids formed by three-dimensional culture directly into a living body in a state of being encapsulated in the gel, so improvement of the engraftment rate of the cells to the living body can be expected.

In the gel composition of the present invention, if the concentration of the amphiphilic polymer decreases, the interaction between the adjacent polymers is weakened so that the gel is likely to be degraded. If a gel composition encapsulating cells is transplanted into a living body, the concentration of the polymer in the gel composition is reduced by water in the living body. Therefore, the gel is degraded, and promotion of cell survival can be expected.

Even in the case of recovering cells after culture, the gel is easily degraded by adding water or an aqueous solution to the gel to reduce the concentration, so that the cells can be easily recovered. For example, it is possible to culture cells in a hydrogel, then to add water in a medium or the like to the hydrogel or to dissolve the gel by pipetting, and then to centrifuge the solution, thereby recovering the cells.

EXAMPLES

Hereinafter, the present invention will be described in more detail by way of examples, but the present invention is not limited to these examples.

[Preparation of Zerogel]

With reference to the method described in WO2009/148121, sarcosine anhydride and aminated poly-L-lactic acid were used as monomer components, and glycolic acid, O-(benzotriazol-1-yl)-N,N,N',N'-tetramethyluronium hexafluorophosphate (HATU) and N, N-diisopropylethylamine (DIEA) were used to synthesize a linear amphiphilic block polymer ($PLA_{32}$-$PSar_{108}$) having a hydrophilic block consisting of 108 sarcosine units and a hydrophobic block consisting of 32 L-lactic acid units.

A 5-fold amount, by weight, of ethanol was added to the polymer obtained above, and the mixture was heated at 70° C. to dissolve the polymer, thereby obtaining a milky white solution. Into each well of a 24-well plate, 600 mg (100 mg of polymer) of this solution was added, and the solvent was removed by air drying overnight in a safety cabinet, thereby obtaining a dry gel (xerogel).

Experiment Example 1

Culture of HepG2 Cell

In Experimental Example 1, HepG2 cells were cultured using the above gel substance as a culture substrate, and observation of the cultured cells and quantification of the gene expression level were performed.

Experimental Example 1-1

Determination of RNA of HepG2 Cultured Cell

When $2.5 \times 10^4$ cells/500 µL of a HepG2 cell suspension was added per well to the xerogel on the well obtained above, the gel absorbed water and a translucent hydrogel was obtained. For comparison, 250 µL of a self-assembled peptide-containing hydrogel ("PuraMatrix", 3D Matrix, Ltd.) was loaded in each well, and $2.5 \times 10^4$/500 µL of a HepG2 cell suspension was added per well.

These samples were cultured at 37° C. in a 5% $CO_2$ environment. After 2 days, 500 µL of a phosphate buffered saline (PBS) was added to each of the wells for the hydrogel obtained from the amphiphilic block polymer and the wells for PuraMatrix. Mixing was performed by pipetting on the wells, and then the whole volume was transferred to a 1.5-mL microtube. Centrifugation was performed to recover the precipitate, and RNA was recovered using QIAGEN RNeasy Kit. The total RNA concentration was measured by fluorescence measurement ("Qbit", Thermo Fisher Scientific Co., Ltd.). The total RNA concentration was also measured by the same procedure, also for samples obtained 3 days and 7 days after the start of culture.

In the wells for the hydrogel obtained from the amphiphilic block polymer (PSar-PLLA), the RNA concentrations were 5.0 ng/µL, 11.6 ng/µL and 92.6 ng/µL after 2 days, 3 days and 7 days, respectively. The amount of the recovered RNA increased with the passage of days. From this result, the proliferation of the cells was confirmed in the gel composition of the present invention.

On the other hand, in the wells for PuraMatrix, the RNA concentrations after 2 days, 3 days and 7 days were all below the detection limit. In the gel composition of the present invention, the gel was degraded (dissolved) by the decrease of the polymer concentration involved in the addition of PBS, and the cells encapsulated in the gel could be recovered. On the other hand, it is considered that, in PuraMatrix, the gel was difficult to be degraded because the self-aggregation ability of the peptide was maintained even though the concentration was lowered, and thus that the cells in the gel could not be taken out.

Experimental Example 1-2

Observation of HepG2 Cultured Cell

In the same manner as in Experimental Example 1-1, after preparing a xerogel of an amphiphilic polymer on the wells and adding a HepG2 cell suspension, the cells were cultured at 37° C. in a 5% $CO_2$ environment, and, after 2 days and 7 days, the observation was made with an inverted microscope. For comparison, a sample obtained by loading 250 µL of an animal-derived ECM-based hydrogel (10-fold dilution from "Matrigel" manufactured by Corning Inc.) in each well and adding a HepG2 cell suspension thereon and a sample obtained by adding a HepG2 cell suspension on a polystyrene plane culture substrate were cultured under the same conditions and observed with an inverted microscope.

Figure 2:
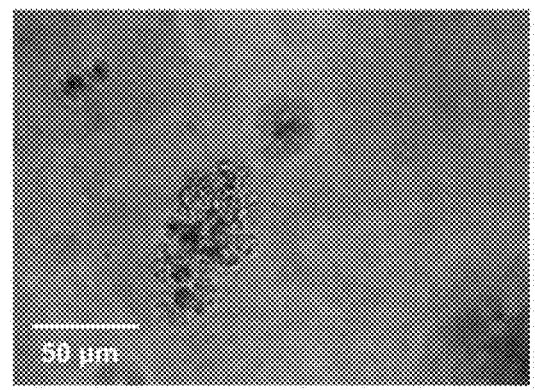
FIG. 2 shows a micrograph of cells cultured using a hydrogel composed of Psar-PLLA in the z direction.

The microscopic observation images 2 days and 7 days after the start of culture of the respective samples are shown in FIG. 1. In plane culture (2D), it was observed that the cells proliferated in a plane, while in the sample cultured on Matrigel, it was observed that a part of the cells became clumps. In the sample cultured on the gel of the amphiphilic polymer (PSar-PLLA), a plurality of cell clumps (spheroids) were observed 2 days after the start of culture (Day 2), and the cell clumps had grown 7 days after the start of culture (Day 7). When the observation position of the inverted microscope was changed to the z direction and the cells indicated by the white arrow in the sample after 7 days were observed, it was confirmed that the cells proliferated three-dimensionally in the gel as shown in FIG. 2.

Experimental Example 1-3

Expression Level of CYP3A4 Gene in HepG2 Cultured Cell

After culturing for 2 days with the amphiphilic polymer (PSar-PLLA) gel, Matrigel and plane culture substrate in the same manner as in Experimental Example 1-2, RNA was recovered by QIAGEN RNeasy Kit in the same manner as in Experimental Example 1-1. The expression level of mRNA encoding CYP3A4 in the recovered RNA was examined by the following procedures. From the recovered RNA, 50 ng was collected, and reverse transcription was performed using a cDNA Reverse Transcription Kit (Thermo Fisher Scientific Co., Ltd.) to prepare cDNA. Real time PCR was performed by TaqMan PCR using a primer specifically amplifying the cDNA of CYP3A4 and a probe specifically binding to the CYP3A4 gene. As an internal control, the gene expression level of GAPDH was determined, and the relative value of the mRNA expression level of CYP3A4 to the mRNA expression level of GAPDH was determined. The average at N=3 was determined for each of the amphiphilic polymer (PSar-PLLA) gel, Matrigel and plane culture substrate. The results are shown in FIG. 3.

Figure 3:
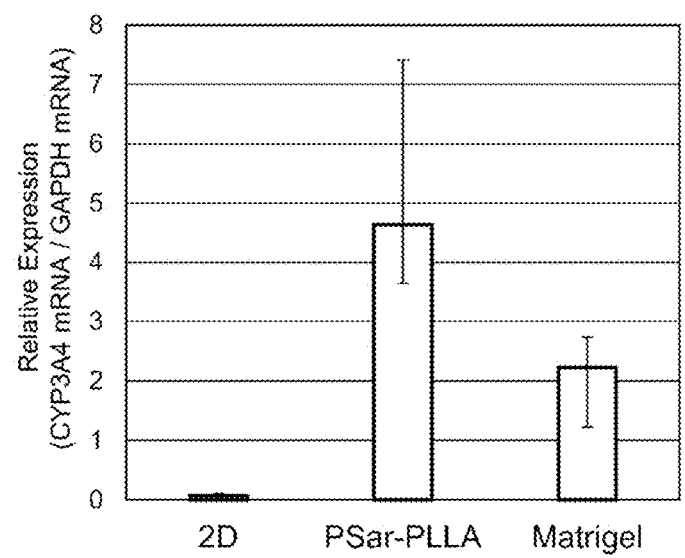
FIG. 3 shows the results of measurement of the expression level of CYP3A4 gene in Experimental Example 1-3.

As shown in FIG. 3, in the culture group using the amphiphilic polymer gel, the expression of the CYP3A4 gene was improved by about 60 times in comparison with the plane culture group. In comparison with the culture group using Matrigel, the expression level of CYP3A4 gene was improved.

Experimental Example 2

Observation of Primary Cultured Stem Cell and CYP3A4 Gene Expression Level

In Experimental Example 2, the same experiments as in Experimental Examples 1-2 and 1-3 described above were performed using, as a target to be cultured, human-derived primary cultured hepatocytes closer to living bodies as a liver-specific functional expression model, instead of the HepG2 cells.

When a xerogel of the amphiphilic polymer was prepared on the wells and 2×10$^5$ cells/500 µL of a primary cultured hepatocyte suspension was added to each well in the same manner as in Experimental Example 1, the gel absorbed water and a translucent hydrogel was obtained. The cells were cultured at 37° C. in a 5% $CO_2$ environment, and observed with an inverted microscope after 1 day, 3 days, and 7 days. Further, in the same manner as in Experimental Example 1-3, RNA was extracted from each cultured cell 1 day, 2 days and 3 days after the start of culture, and the relative value of the mRNA expression level of CYP3A4 to the mRNA expression level of GAPDH was determined.

For comparison, a sample obtained by loading 250 µl of a 10-fold diluted solution of Matrigel in each well and adding a primary cultured hepatocyte suspension thereon, a sample obtained by adding a primary cultured hepatocyte suspension on a commercially available three-dimensional spheroid formation microplate (Corning Inc., product number 4515), and a sample obtained by adding a primary cultured hapatocyte suspension on a polystyrene plane culture substrate were cultured under the same conditions. Observation with an inverted microscope and quantification of the gene expression level were performed.

Figure 4:
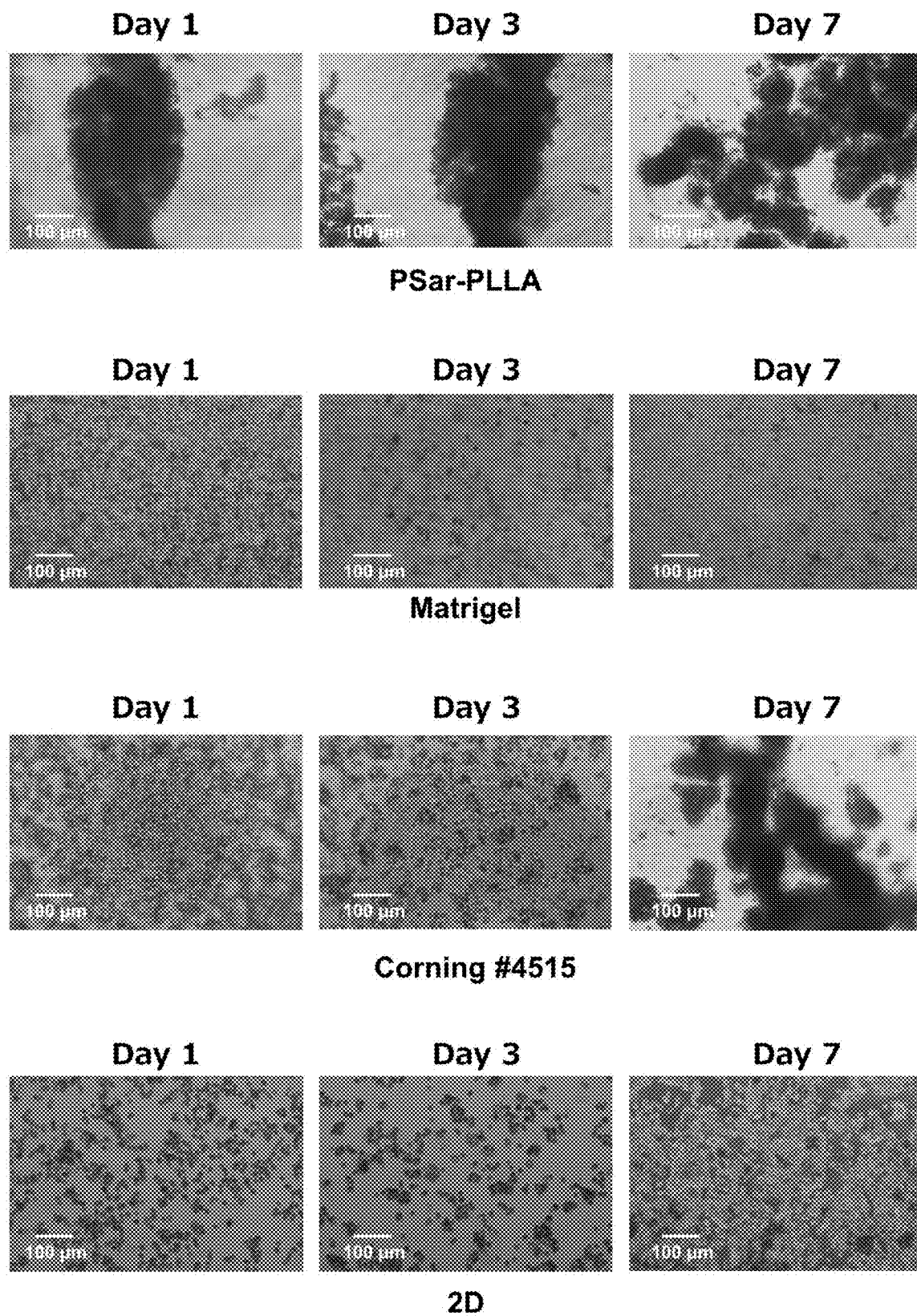
FIG. 4 shows microscopic images of Experimental Example 2.
Figure 5:
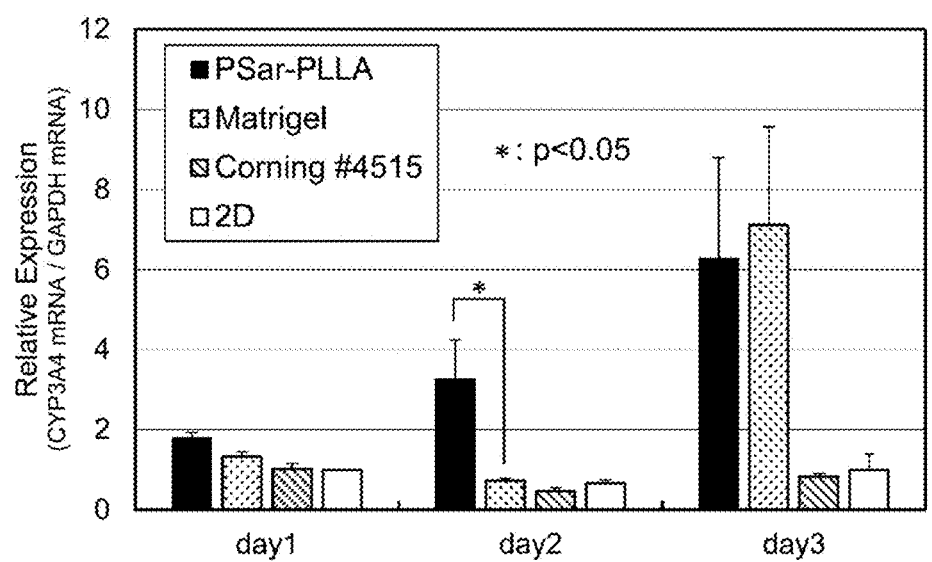
FIG. 5 shows the results of measurement of the expression level of CYP3A4 gene in Experimental Example 2.

The microscopic observation images of Experimental Example 2 are shown in FIG. 4, and the relative value (average at N=3) of the mRNA expression level of CYP3A4 to the mRNA expression level of GAPDH is shown in FIG. 5.

As shown in FIG. 4, it was observed that the cells proliferated chronologically in all the culture samples. One day after the start of culture (Day 1), spheroids of 200 µm or more were observed in the sample cultured on the gel of the amphiphilic polymer (PSar-PLLA), while no spheroid was observed in the other culture samples. In the sample using the spheroid formation microplate (Corning #4515), spheroids smaller than 100 µm were observed 3 days after the start of culture (Day 3), and the size of the spheroids became 100 µm or more after 7 days (Day 7). In the sample cultured on Matrigel, it was observed that the cells adhered to the bottom of the plate 7 days after the start of culture. In the sample cultured on the amphiphilic polymer gel, it was observed that the spheroids were divided 7 days after the start of the culture.

In FIG. 5, no clear difference was found among the four culture groups 1 day after the start of culture, but, after 2 days, the expression level of CYP3A4 gene in the culture group using the amphiphilic polymer gel was about 5 times higher than that in the plane culture group, about 4.5 times higher than that in the culture group using Matrigel, and about 7 times higher than that in the culture group using the spheroid formation microplate, and a significant difference was observed at a risk factor of 5%. Three days after the start of culture, the expression level of CYP3A4 gene in the culture group using the amphiphilic polymer gel was almost equal to that in the culture group using Matrigel.

From the above results, it can be seen that the gel having the amphiphilic block polymer as a component is useful as a substrate for three-dimensional culture of various cells. It can be seen that, in the gel composed of the amphiphilic block polymer, cell spheroids are formed three-dimensionally in a short period of time in comparison with the conventional three-dimensional culture substrate, and high-function cultured cells equivalent in functions to the cells in a living body can be obtained.

The invention claimed is:

1. A method for producing a gel composition for cell culture, the method comprising:
   mixing an amphiphilic block polymer having a hydrophilic block chain and a hydrophobic block chain with an organic solvent to prepare an organogel; and
   removing the organic solvent from the organogel to form a xerogel,
   wherein the amphiphilic block polymer has 20 or more sarcosine units in the hydrophilic block and 10 or more lactic acid units in the hydrophobic block chain.

2. The method for producing a gel composition for cell culture according to claim 1, wherein the organic solvent contains an alcohol having 1 to 6 carbon atoms.

3. The method for producing a gel composition for cell culture according to claim 1, wherein the organic solvent is removed from the organogel on a substrate for cell culture to form the xerogel on the substrate for cell culture.

4. A method for producing a gel composition for cell culture, the method comprising:
   forming the xerogel by the method according to claim 1; and
   mixing the xerogel with water or an aqueous solution to form a hydrogel.

5. The method for producing a gel composition for cell culture according to claim 4, wherein the aqueous solution contains cells to be cultured, and the xerogel and the aqueous solution are mixed to form a hydrogel encapsulating the cells.

6. The method for producing a gel composition for cell culture according to claim 1, wherein the amphiphilic block polymer has 25 to 200 sarcosine units in the hydrophilic block and 10 to 1000 lactic acid units in the hydrophobic block chain.

7. The method for producing a gel composition for cell culture according to claim 1, wherein the amphiphilic block polymer has 30 to 150 sarcosine units in the hydrophilic block and 15 to 500 lactic acid units in the hydrophobic block chain.

8. The method for producing a gel composition for cell culture according to claim 1, wherein the amphiphilic block polymer has 30 to 150 sarcosine units in the hydrophilic block and 20 to 100 lactic acid units in the hydrophobic block chain.

9. The method for producing a gel composition for cell culture according to claim 1, wherein the amphiphilic block polymer has 25 to 200 sarcosine units in the hydrophilic block and 20 to 100 lactic acid units in the hydrophobic block chain.

10. The method for producing a gel composition for cell culture according to claim 1, wherein the amphiphilic block polymer has 25 to 200 sarcosine units in the hydrophilic block and 15 to 500 lactic acid units in the hydrophobic block chain.

11. The method for producing a gel composition for cell culture according to claim 1, wherein the hydrophobic block chain further includes a monomer unit including at least one selected from a hydroxy acid, a hydrophobic amino acid, or an amino acid derivative.

12. The method for producing a gel composition for cell culture according to claim 11, wherein the hydrophobic block chain includes the monomer unit that includes the hydroxy acid, and the hydroxy acid includes glycolic acid, hydroxyisobutyric acid, or both.

13. The method for producing a gel composition for cell culture according to claim 11, wherein the hydrophobic block chain includes the monomer unit that includes the hydrophobic amino acid, and the hydrophobic amino acid includes at least one selected from glycine, alanine, valine, leucine, isoleucine, proline, methionine, tyrosine, or tryptophan.

14. The method for producing a gel composition for cell culture according to claim 11, wherein the hydrophobic block chain includes the monomer unit that includes the amino acid derivative, and the amino acid derivative includes at least one selected from glutamic acid methyl ester, glutamic acid benzyl ester, aspartic acid methyl ester, aspartic acid ethyl ester, or aspartic acid benzyl ester.

15. The method for producing a gel composition for cell culture according to claim 1, wherein the hydrophilic block chain further includes a monomer unit including at least one selected from a hydrophilic amino acid or an amino acid derivative.

16. The method for producing a gel composition for cell culture according to claim 15, wherein the hydrophilic block chain includes the monomer unit that includes the hydrophilic amino acid, and the hydrophilic amino acid includes at least one selected from serine, threonine, lysine, aspartic acid, or glutamic acid.

17. The method for producing a gel composition for cell culture according to claim 1, wherein the hydrophilic block chain further includes a sugar chain, a polyether, or both.

18. The method for producing a gel composition for cell culture according to claim 1, wherein the organic solvent includes an alcohol having 1 to 4 carbon atoms.

19. The method for producing a gel composition for cell culture according to claim 1, wherein the organic solvent includes at least one selected from include methanol, ethanol, propanol, 2-propanol, butanol, or 2-butanol.

20. The method for producing a gel composition for cell culture according to claim 1, wherein the organic solvent includes ethanol.

\* \* \* \* \*